(12) United States Patent
Foo et al.

(10) Patent No.: US 7,368,492 B2
(45) Date of Patent: May 6, 2008

(54) PROCESS FOR THE SYNTHESIS OF GLYCOLONITRILE

(75) Inventors: Thomas Foo, Wilmington, DE (US); Anna Panova, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 131 days.

(21) Appl. No.: 11/314,386

(22) Filed: Dec. 21, 2005

(65) Prior Publication Data

US 2006/0160196 A1   Jul. 20, 2006

Related U.S. Application Data

(60) Provisional application No. 60/638,127, filed on Dec. 22, 2004.

(51) Int. Cl.
*C08J 5/15* (2006.01)
*C08K 5/49* (2006.01)
*C08L 5/49* (2006.01)

(52) U.S. Cl. ........................ 524/121; 556/174
(58) Field of Classification Search ........... 524/121; 556/174
See application file for complete search history.

(56) References Cited

U.S. PATENT DOCUMENTS

| | | | |
|---|---|---|---|
| 2,175,605 A | | 10/1939 | Jacobson |
| 2,175,805 A | * | 10/1939 | Jacobson .................. 203/8 |
| 2,890,238 A | * | 6/1959 | Sexton .................. 558/351 |
| 5,187,301 A | * | 2/1993 | Cullen et al. ............. 558/455 |
| 5,208,363 A | | 5/1993 | Crump et al. |
| 5,508,181 A | | 4/1996 | Hashimoto |
| 5,756,306 A | | 5/1998 | Yamaguchi et al. |
| 5,817,613 A | | 10/1998 | Athey et al. |
| 6,037,155 A | | 3/2000 | Kobayashi et al. |
| 6,759,549 B2 | | 7/2004 | Stern et al. |
| 2003/0040085 A1 | | 2/2003 | Aoki et al. |

FOREIGN PATENT DOCUMENTS

FR   1 575 475   7/1969
JP   2003192655   * 7/2003

* cited by examiner

*Primary Examiner*—Sikarl A. Witherspoon
*Assistant Examiner*—Chukwuma O. Nwaonicha
(74) *Attorney, Agent, or Firm*—Christine M. Lhulier

(57) ABSTRACT

A process to prepare substantially pure glycolonitrile in an aqueous medium is provided by reacting hydrogen cyanide and formaldehyde. The formaldehyde feed stream is heated prior to reacting with hydrogen cyanide, resulting in an aqueous glycolonitrile solution with fewer impurities, especially less unreacted formaldehyde, than is obtained by other methods. The process enables production of an aqueous glycolonitrile solution that requires less post-reaction purification (if any at all) prior to enzymatically converting the glycolonitrile into glycolic acid.

18 Claims, 7 Drawing Sheets

PROCESS FOR THE SYNTHESIS OF GLYCOLONITRILE

This application claims the benefit of U.S. Provisional Application No. 60/638,127, filed Dec. 22, 2004.

FIELD OF THE INVENTION

This invention relates to a chemical process to synthesize glycolonitrile from formaldehyde and hydrogen cyanide. More specifically, a method to produce substantially pure glycolonitrile is provided by reacting pre-heated formaldehyde with hydrogen cyanide.

BACKGROUND OF THE INVENTION

Glycolonitrile (HOCH$_2$CN; CAS Registry Number 107-16-4) is an α-hydroxynitrile that can be enzymatically converted to glycolic acid using a catalyst having nitrilase activity or a combination of nitrile hydratase and amidase activities. Glycolic acid (HOCH$_2$CO$_2$H; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, and as a component in personal care products like skin creams. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]).

Glycolonitrile is also a versatile intermediate in the preparation of aminonitriles, which are, in turn, useful in preparing aminocarboxylic acid compounds. For example, U.S. Pat. No. 5,208,363 discloses the use of glycolonitrile in the preparation of aminonitrile precursors for the production of ethylenediaminetetraacetic acid (EDTA), and U.S. Pat. No. 5,817,613 describes the use of glycolonitrile in the synthesis of 2-hydroxyethyl iminodiacetic acid (HEIDA). EDTA and HEIDA are useful as chelating agents as components of detergent compositions. FR1575475 describes the use of glycolonitrile in the synthesis of alkali metal salts of nitrilotriacetic acid. In addition, glycolonitrile can be used as a precursor to glycinonitrile, which can be converted to glycine as disclosed in US2003/0040085. Glycine is widely used as an additive in processed meats and beverages, and as a raw material for the commercially important herbicide, N-(phosphonomethyl)glycine, also known by its common name glyphosate, as described in U.S. Pat. No. 6,759,549.

Microbial catalysts can hydrolyze a nitrile (e.g., glycolonitrile) directly to the corresponding carboxylic acids (e.g., glycolic acid) using a nitrilase (EC 3.5.5.7), where there is no intermediate production of the corresponding amide (Equation 1), or by a combination of nitrile hydratase (EC 4.2.1.84) and amidase (EC 3.5.1.4) enzymes, where a nitrile hydratase (NHase) initially converts a nitrile to an amide, and then the amide is subsequently converted by the amidase to the corresponding carboxylic acid (Equation 2):

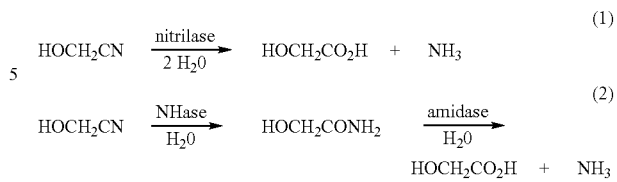

Enzymatic synthesis of glycolic acid requires a substantially pure form of glycolonitrile. Methods to synthesize glycolonitrile by reacting aqueous solutions of formaldehyde and hydrogen cyanide have previously been reported (U.S. Pat. No. 2,175,805; U.S. Pat. No. 2,890,238; and U.S. Pat. No. 5,187,301; Equation 3).

Concentrated aqueous solutions of formaldehyde (e.g., 37 wt % solutions commercially known as formalin) typically are comprised of free formaldehyde and various oligomers of formaldehyde (for example, paraformaldehyde and trixoxymethylene). The presence of formaldehyde oligomers can influence overall conversion to glycolonitrile. Hence, a method to pre-treat the formaldehyde that transforms formaldehyde oligomers to more free formaldehyde in the feed stream prior to reacting with hydrogen cyanide should increase the yield of glycolonitrile and should decrease the conversion of unwanted secondary products produced from the oligomers.

Jacobson (U.S. Pat. No. 2,175,805) discloses a method of obtaining pure glycolonitrile by the reaction of hydrogen cyanide and formaldehyde in the presence of an acidic compound followed by distillation at subatmospheric pressure (vacuum distillation step conducted at about 125° C.). The reactants are preferably mixed "in the cold" (i.e., below 26° C. to maintain the hydrogen cyanide in liquid form). Also described in U.S. Pat. No. 2,175,805 is the observation that 1) glycolonitrile decomposes at ambient temperature, and 2) glycolonitrile contacted with bases decomposes violently within hours at ambient temperature. Jacobson does not disclose pre-treatment of the concentrated aqueous formaldehyde feed prior to reacting with hydrogen cyanide.

Sexton (U.S. Pat. No. 2,890,238) discloses a method of preparing glycolonitrile in which formaldehyde is fed into an aqueous solution of HCN. The reaction is run "with efficient reflux or a closed pressure system, with the reaction allowed to go as high as 100° C." However, as described in Jacobson, glycolonitrile decomposes at room temperature. A reaction run at temperatures as high as 100° C. would be expected to result in an increase in the decomposition of the glycolonitrile. Similar to Jacobson, Sexton does not describe a method to pre-treat the formaldehyde prior to reacting with hydrogen cyanide.

Cullen etal. (U.S. Pat. No. 5,187,301) discloses a method for making iminodiacetonitrile from glycolonitrile. This reference describes how glycolonitrile can be formed in a process (either batch or continuous) by maintaining the pH of the formaldehyde above about 3, preferably in the range of about 5-7, most preferably about 5.5, with suitable acids and bases. The formaldehyde is then reacted with hydrogen cyanide in a temperature range of about 20 to 80° C., preferably about 30° C., to form glycolonitrile. However, as shown in the present examples, a reaction run within the conditions specified in Cullen et al. results in a significant amount of unreacted free formaldehyde after 2 hours of reaction time.

All of the above mentioned methods produce a purity of glycolonitrile that typically requires extensive processing steps, such as distillative purification, to remove some of the secondary products (impurities). Many of the impurities found in glycolonitrile, such as unreacted formaldehyde, have been reported to interfere with the enzymatic conversion to glycolic acid by inactivating the enzyme catalyst (U.S. Pat. No. 5,756,306; U.S. Pat. No. 5,508,181; and U.S. Pat. No. 6,037,155; hereby incorporated in their entirety by reference).

The problem to be solved is the lack of a method to produce glycolonitrile by reacting formaldehyde and hydrogen cyanide under conditions that produce a substantially pure reaction product. Specifically, a method is lacking that reduces the amount of unreacted formaldehyde (one of the impurities associated with enzyme inactivation when converting glycolonitrile to glycolic acid), and minimizes the number of post-reaction purification steps.

SUMMARY OF THE INVENTION

A method for preparing glycolonitrile is provided comprising:
 (a) providing an aqueous formaldehyde feed stream that is heated to a temperature of about 90° C. to about 150° for a determinable period of time; and
 (b) reacting the heated aqueous feed stream of (a) with hydrogen cyanide at a temperature suitable for glycolonitrile synthesis, whereby glycolonitrile is produced.

In one embodiment, the glycolonitrile produced by the present process is recovered.

The amount of time the aqueous formaldehyde feed stream is heated may vary as long as the polymeric formaldehyde impurities are substantially decomposed into monomeric formaldehyde prior to reacting the heated aqueous stream with hydrogen cyanide. In one embodiment, the aqueous formaldehyde feed stream is heated to a temperature of about 90° C. to about 150° C. for a period of time from about 10 seconds to about 24 hours. In another embodiment, the period of heating may range from about 30 seconds to about 6 hours. The method further comprises the addition of catalytic amounts of base, such as NaOH or KOH, to accelerate the conversion of higher molecular weight polymeric formaldehyde into lower molecular weight and monomeric formaldehyde. In a further embodiment, the heated formaldehyde is promptly fed to the reactor and reacted with hydrogen cyanide.

The heated aqueous formaldehyde feed stream is promptly fed to a reaction chamber pre-charged with hydrogen cyanide at a temperature suitable for glycolonitrile synthesis. In one embodiment, the reaction temperature is typically about 70° C. or less in order to minimize glycolonitrile decomposition. In another embodiment, the reaction temperature is between about −20° C. to about 70° C., preferably about 0° C. to about 70° C., more preferably about 0° C. to about 55° C., even more preferably about 10° C. to about 30° C., and most preferably about 20° C. to about 25° C.

Additional embodiments of the invention include the aqueous formaldehyde feed stream further comprising about 0.1 wt % to about 15 wt % methanol, or about 3 wt % to about 8 wt % methanol. The method further comprises adding glycolic acid to the aqueous glycolonitrile to maintain the pH of the glycolonitrile below 7. The resulting product may be recovered, isolated, and/or purified.

BRIEF DESCRIPTION OF THE FIGURES

FIG. 4 also clearly shows the resonance at δ49 ppm for the methanol from the formalin feed used in Example 3.

DETAILED DESCRIPTION OF THE INVENTION

Figure 1:
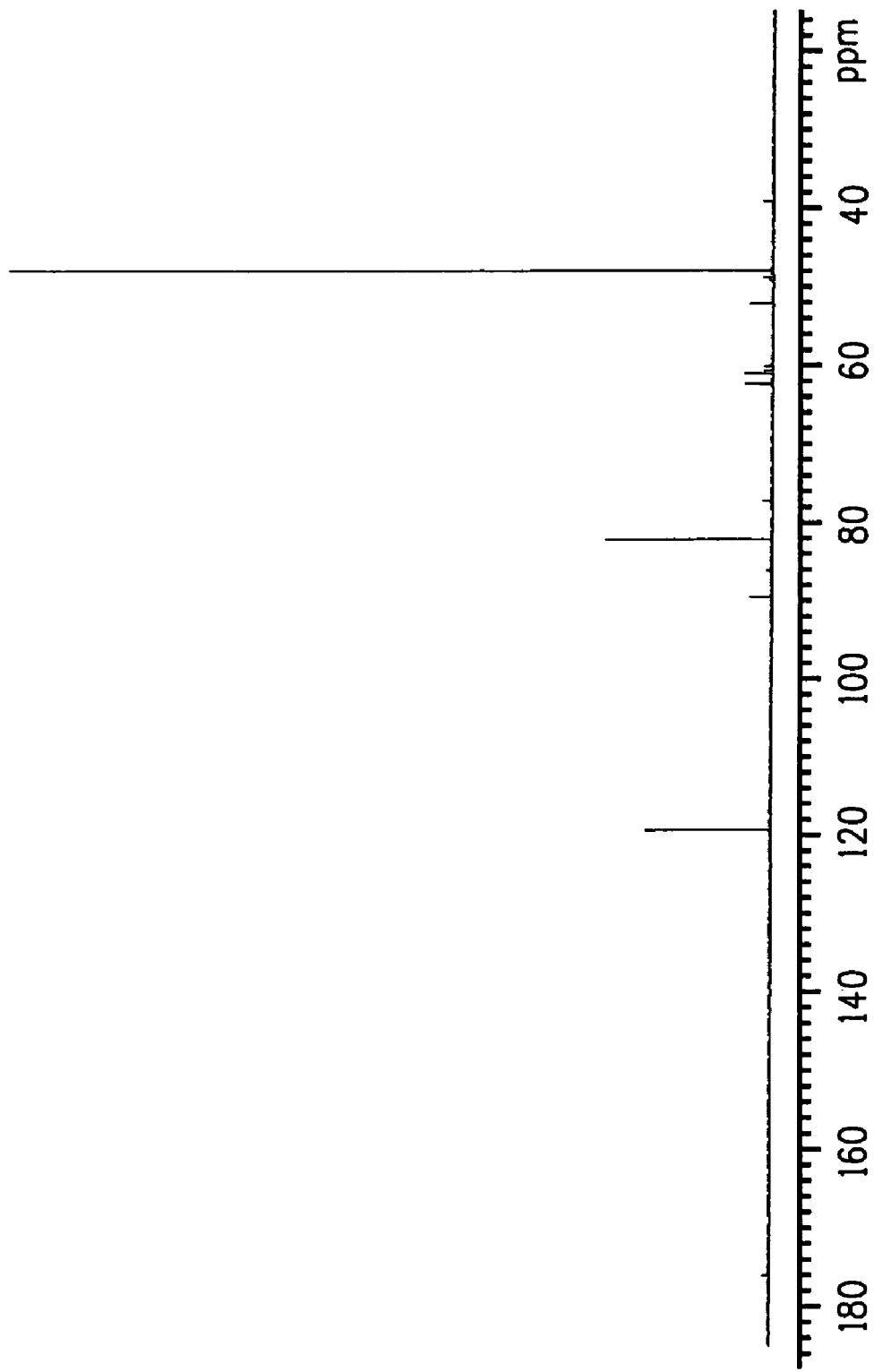
FIG. 1 shows $^{13}$C NMR spectrum of the resulting glycolonitrile solution from Comparative Example A, qualitatively indicating the purity of the glycolonitrile product. The $^{13}$C NMR spectrum shows the major glycolonitrile $^{13}$C resonances at about δ48 and 119 ppm. There are also substantial resonances around δ80-90 ppm for unreacted formaldehyde and around δ60 ppm for other by-product species derived from unreacted formaldehyde.

The stated problem has been solved by providing a method that produces an aqueous solution comprising glycolonitrile with significantly fewer impurities, especially unreacted free formaldehyde, than can be obtained by other methods. Specifically, the aqueous formaldehyde feed stream is heat-treated prior to the reaction with hydrogen cyanide. The reaction yields very high formaldehyde conversion and few accompanying impurities.

Concentrated aqueous formaldehyde solutions are typically comprised of monomeric formaldehyde ("free formaldehyde", the desired substrate for the reaction) and oligomers of formaldehyde. Pre-heating the formaldehyde feed stream improves the purity of the resulting glycolonitrile product. The reaction of formaldehyde with hydrogen cyanide is temperature-controlled to minimize glycolonitrile decomposition. The reaction product formed is an aqueous solution comprising glycolonitrile and significantly less unreacted formaldehyde when compared to a reaction product obtained without pre-heating the aqueous formaldehyde feed stream.

The resulting aqueous glycolonitrile solution requires fewer post reaction purification steps (such as distillative purification), thus reducing the cost of producing glycolonitrile that is suitable for uses requiring a certain level of purity, such as, enzymatic synthesis of glycolic acid. Additionally, reducing the amount of unreacted formaldehyde in the aqueous glycolonitrile solution used for enzymatic synthesis of glycolic acid should extend the enzymatic catalyst's lifespan (i.e., the number of recycle reactions). This improves the catalyst's productivity and reduces the cost for preparing glycolic acid. The invention yields a glycolonitrile product that may be used directly for enzymatic conversion without purification, significantly reducing the cost of producing glycolic acid.

Aqueous formaldehyde (ranging in concentration from about 5 wt % to about 70 wt %; preferably about 20 wt % to about 55 wt %) is heated to a temperature ranging from about 35° C. to about 200° C.; preferably about 90° C. to about 150° C. The heated aqueous formaldehyde feed stream is promptly fed to a reaction chamber pre-charged with hydrogen cyanide at a temperature suitable for glycolonitrile synthesis. As used herein, the term "a temperature suitable for glycolonitrile synthesis" is used to describe a reaction temperature range suitable for reacting hydrogen cyanide and the heat-treated formaldehyde. In one embodiment, the reaction temperature is typically about 70° C. or less in order to minimize glycolonitrile decomposition. In another embodiment, the reaction temperature is between about −20° C. to about 70° C., preferably about 0° C. to about 70° C., more preferably about 0° C. to about 55° C., even more preferably about 10° C. to about 30° C., and most preferably about 20° C. to about 25° C.

The heated aqueous formaldehyde and the hydrogen cyanide are added to the reaction mixture at a rate to ensure 1) the hydrogen cyanide is in slight excess (at least 1% molar excess compared to the amount of formaldehyde added; preferably at least 10% excess), and 2) the overall reaction temperature is maintained at a temperature suitable for glycolonitrile synthesis. The resulting aqueous solution of glycolonitrile is significantly purer (i.e., has less unreacted formaldehyde), requiring less post-reaction purification.

In another embodiment, the aqueous glycolonitrile reaction product formed does not require any post-reaction purification prior to enzymatic conversion to glycolic acid.

Definitions:

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one aspect, the term "about" means within 20% of the recited numerical value, preferably within 10%, and most preferably within 5%.

The term "glycolonitrile" is abbreviated as "GLN" and is synonymous with hydroxyacetonitrile, 2-hydroxyacetonitrile, hydroxymethylnitrile, and all other synonyms of CAS Registry Number 107-16-4.

The term "glycolic acid" is abbreviated as "GLA" and is synonymous with hydroxyacetic acid, hydroxyethanoic acid, and all other synonyms of CAS Registry Number 79-14-1.

The term "formaldehyde" is abbreviated as "FA" and is synonymous with formic aldehyde, methyl aldehyde, oxomethane, and all other synonyms of CAS Registry Number 50-00-0. Commercially available formaldehyde is typically comprised of a mixture of monomeric formaldehyde ("free formaldehyde") and various oligomers of formaldehyde. As used herein, the term "free formaldehyde" refers to monomeric formaldehyde.

The term "hydrogen cyanide" is synonymous with prussic acid, hydrocyanic acid, and all other synonyms of CAS Registry Number 200-821-6.

As used herein, the terms "heat treatment", "heat-treated", "heating the formaldehyde feed stream", "pre-heated formaldehyde", and "an aqueous formaldehyde feed stream that is heated" are used to describe the process of subjecting an aqueous formaldehyde solution to a prescribed temperature for a period of time prior to reacting with hydrogen cyanide. The temperature and duration of the heat treatment is chosen to optimize the amount of monomeric formaldehyde in the heated formaldehyde feed stream. In one embodiment, the aqueous formaldehyde solution is heat-treated at a temperature from about 35° C. to about 200° C., preferably from about 75° C. to about 150° C., more preferably from about 90° C. to about 150° C., and most preferably from about 100° C. to about 125° C. for a determinable period of time, ranging from about 10 seconds to about 24 hours, preferably from about 10 seconds to about 6 hours, and more preferably about 10 seconds to about 20 minutes, and most preferably about 2 minutes to about 10 minutes. In one embodiment, the heat treatment time is about 2 minutes to about 10 minutes in the presence of a base catalyst. The heated formaldehyde is promptly fed to the reactor and reacted with hydrogen cyanide.

As used herein, the terms "promptly fed to the reactor" and "promptly adding the heated formaldehyde" are used to described the time period between the end of the heat treatment period and the initiation of the reaction with hydrogen cyanide, typically less than about 24 hours, preferably less than about 1 hour, more preferably less than about 15 minutes, most preferably less than about 5 minutes. Optionally, the time between the end of heat treatment period and the initiation of the hydrogen cyanide reaction may be more than about 24 hours.

Suitable Reaction Conditions:

The present method describes a process to produce aqueous glycolonitrile by reacting formaldehyde and hydrogen cyanide. The formaldehyde is heated prior to reacting with the hydrogen cyanide to make glycolonitrile. The starting concentration of the formaldehyde is typically an aqueous solution of about 5 wt % to about 70 wt %. In one embodiment, the formaldehyde feed stream is comprised of about 20 wt % to about 55 wt % formaldehyde. In another embodiment, the formaldehyde feed stream is comprised of about 37 wt % formaldehyde. The formaldehyde feed stream may optionally be comprised of about 0.1 wt % to about 15 wt % (typically 6-8 wt %) methanol (an additive typically found in some 37 wt % solutions [i.e.,formalin]).

A base catalyst (KOH, NaOH, etc.) may be added to the aqueous formaldehyde solution prior to heating the aqueous formaldehyde feed stream. As exemplified herein, sodium hydroxide may be added to the aqueous formaldehyde feed stream prior to heating the formaldehyde feed stream. In one embodiment, the molar ratio of NaOH:formaldehyde in the heated aqueous formaldehyde feed stream is about 1:50 to about 1:2000. In another embodiment, the molar ratio of NaOH:HCHO in the heated aqueous formaldehyde feed stream is about 1:100 to about 1:2000.

The formaldehyde feed stream is heated to a temperature of about 35° C. to about 200° C. for a determinable period of time. In one embodiment, the formaldehyde feed stream is heated to a temperature of about 75° C. to about 150° C. In another embodiment, the formaldehyde feed stream is heated to a temperature of about 90° C. to about 150° C. In yet another embodiment, the formaldehyde feed stream is heated to a temperature of about 100° C. to about 125° C. As used herein, the term "determinable period of time" is used to describe the amount of time the formaldehyde feed stream is heated to the specified temperature. The optimal length of time the formaldehyde is heat-treated can be easily determined and may be adjusted depending upon the selected temperature in combination with the specific design of the heat treatment system and the reactor. The length of the heat treatment is chosen to maximize the amount of monomeric formaldehyde in the heated feed stream. The monomeric formaldehyde reacts with the hydrogen cyanide to produce a glycolonitrile solution with substantially fewer impurities (i.e. unreacted formaldehyde and impurities associated with polymeric forms of formaldehyde). Typically, the heat treatment period can last from about 10 seconds to about 24 hours, preferably about 10 seconds to about 6 hours, more preferably about 10 seconds to about 20 minutes, and most preferably about 2 minutes to about 10 minutes. In one embodiment, the heat treatment time is about 2 minutes to about 10 minutes in the presence of a base catalyst. The heated formaldehyde is then promptly fed to the reaction chamber.

The hydrogen cyanide feed stream is typically added at a rate sufficient to maintain a slight molar excess of hydrogen cyanide relative to the amount of formaldehyde added to the reaction chamber. In one embodiment, the molar ratio of hydrogen cyanide to formaldehyde is at least about 1.01:1, preferably no greater than about 10:1. In another embodiment, the molar ratio of HCN to formaldehyde is about 1.01:1, more preferably no greater than about 2:1. In a further embodiment, the molar ratio of HCN to formaldehyde is about 1.05:1 to about 1.15:1.

The reaction chamber may optionally be pre-charged with hydrogen cyanide so that the formaldehyde is immediately in contact with the hydrogen cyanide upon addition to the reaction chamber. Pre-charging the reaction chamber with hydrogen cyanide aids in maintaining the slight excess of hydrogen cyanide during the reaction. One skilled in the art recognizes that when an HCN pre-charge is used, the mole ratio of the HCN to formaldehyde rapidly transitions from infinity to the more sustainable ration of 10:1 or less, preferably 2:1 or less, more preferably about 1.01:1 to about 1.15:1, and most preferably about 1.01:1 to about 1.05:1.

The temperature of the reaction chamber is typically about 70° C. or less in order to minimize glycolonitrile decomposition. In another embodiment, the reaction temperature is between about −20° C. to about 70° C., preferably about 0° C. to about 70° C., more preferably about 0° C. to about 55° C., even more preferably about 10° C. to about 30° C., and most preferably about 20° C. to about 25° C.

Atmospheric pressure is satisfactory for carrying out the reaction of formaldehyde and hydrogen cyanide, and hence pressures of from about 0.5 to about 10 atmospheres (50.7 kPa to 1013 kPa) are preferred. Higher pressures, up to 20,000 kPa or more may be used, if desired, but any benefit that may be obtained thereby would probably not justify the increased cost of such operations.

The pH in the glycolonitrile synthesis reaction chamber is about 3 to about 10, preferably about 5 to about 8.

The present glycolonitrile synthesis reaction can be run in continuous, batch, or fed batch mode. The fed batch reaction typically is run for about 10 seconds to about 24 hours, preferably about 30 minutes to about 8 hours, more preferably about 0.5 hours to about 4 hours.

Analytical Methods

A variety of analytical methods can be used in the present methods to analyze the reactants and products including, but not limited to titration, high performance liquid chromatography (HPLC), gas chromatography (GC), mass spectroscopy (MS), quantitative $^{13}C$ nuclear magnetic resonance (NMR), and capillary electrophoresis (CE), to name a few.

Post-Reaction Recovery, Isolation, and/or Purification

The present method produces glycolonitrile with significantly less free (monomeric) formaldehyde. In one embodiment, the glycolonitrile does not require additional purification/isolation/recovery steps prior to being enzymatically converted into glycolic acid (typically in the form ammonium glycolate). In another embodiment, the glycolonitrile produced by the present method can be purified, isolated, and/or recovered using a variety of techniques including, but not limited to distillation, crystallization, and solvent extraction.

Stabilization of Glycolonitrile Under Acidic Conditions

In one embodiment, a mineral acid (e.g., HCl, $H_2SO_4$, or $H_3PO_4$) is added to the glycolonitrile mixture obtained by the present method to maintain the pH of the glycolonitrile below 7 (glycolonitrile has been reported to decompose under basic conditions). In another embodiment, glycolic acid is added to the glycolonitrile mixture obtained by the present method to maintain the pH of the glycolonitrile below 7. In a further embodiment, the amount of glycolic acid added is sufficient to maintain the pH of the glycolonitrile below about 6, preferably below about 5, more preferably below about 4, and most preferably below about 3.5. Stabilization with glycolic acid is a preferred embodiment in the instance where the glycolonitrile is subsequently converted to glycolic acid using an enzyme catalyst. The use of glycolic acid to adjust the pH in this instance avoids the addition of a mineral acid, where, upon conversion of glycolonitrile to glycolic acid, the presence of a mineral acid and/or the production of the corresponding mineral acid salt may require a purification step to remove the mineral acid and/or the corresponding salt from the glycolic acid product. In one embodiment, the pH of the acid-stabilized glycolonitrile solution is adjusted with a base to a more neutral pH range (i.e. pH of about 6 to about 8) prior to enzymatic conversion of glycolonitrile to glycolic acid (typically in the form of the ammonium salt of glycolic acid).

GENERAL METHODS

The following examples are provided to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The abbreviations in the specification correspond to units of measure, techniques, properties, or compounds as follows: "sec" means second(s), "min" means minute(s), "h" or "hr" means hour(s), "cm" means centimeters, "mm" means millimeters, "µL" means microliters, "mL" means milliliters, "L" means liters, "mM" means millimolar, "M" means molar, "mmol" means millimole(s), "wt" means weight, "wt %" means weight percent, "g" means grams, "d" means density in g/mL, "kPa" means kilopascals, "µg" means micrograms, "ID" means internal diameter, "OD" means outside diameter, and "HPLC" means high performance liquid chromatography.

EXAMPLES

Analytical Methodology

HPLC Analysis

The reaction product mixtures were analyzed by the following HPLC method. Aliquots (0.01 mL) of the reaction mixture were added to 1.50 mL of water, and analyzed by HPLC (HPX 87H column, 30 cm×7.8 mm; 0.01 N $H_2SO_4$ mobile phase; 1.0 mL/min flow at 50° C.; 10 µL injection volume; RI detector, 20 min analysis time). The method was calibrated for glycolonitrile at a series of concentrations using commercially available glycolonitrile purchased from Aldrich.

Quantitative $^{13}C$ NMR Analysis

Quantitative $^{13}C$ NMR spectra were obtained using a Varian Unity Inova spectrometer (Varian, Inc., Palo Alto, Calif.) operating at 400 MHz. Samples were prepared by taking 3.0 mL of the reaction product along with 0.5 mL of $D_2O$ in a 10 mm NMR tube. $^{13}C$ NMR spectra were typically acquired using a spectral width of 26 KHz with the transmitter located at 100 ppm, 128K points, and a 90-degree pulse (pw90=10.7 microseconds at a transmitter power of 56 db). The longest 13C T1 (23 sec) was associated with the GLN nitrile carbon, and the total recycle time was set greater than ten times this value (recycle delay d1=240 sec, acquisition time at =2.52 sec). Signal averaging of 360 scans gave a total experiment time of 26.3 hours. The Nuclear Overhauser Enhancement (NOE) was suppressed by gating on the Waltz-modulated 1H decoupling only during the acquisition time (at).

Comparative Example A

Pre-Heating 0% of Formaldehyde

Approximately 10.18 g of 52 wt % aqueous solution of formaldehyde (<1% methanol, E.I. DuPont de Nemours; Wilmington, Del.) was mixed with 12.81 g of water, and the slurry was heated to about 76° C. for about 40 min until the mixture became a clear homogeneous liquid solution. The solution was allowed to cool to ambient temperature and remained a homogeneous liquid. 0.14 mL of 16.7 wt % aqueous NaOH solution was then added to the formaldehyde solution. 1.56 g of the resulting solution (23 wt % formaldehyde) was placed in the reaction vessel, and the remainder was used for the continuous formaldehyde feed.

The reaction vessel, equipped with stirring, was placed within an oil bath maintained at 55° C. The reactants were then each continuously pumped into the reaction vessel over a period of about 2.0 hr, as follows:

4.41 mL/hr of 50 wt % aqueous HCN solution (d=0.86 g/mL)

7.00 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

FIG. 1 shows the $^{13}C$ NMR spectrum of the resulting glycolonitrile solution, qualitatively indicating the purity of the glycolonitrile product. The $^{13}C$ NMR spectrum shows the major glycolonitrile $^{13}C$ resonances at about δ48 and 119 ppm. There are also substantial resonances around δ80-90 ppm for unreacted formaldehyde and around δ60 ppm for other by-product species derived from unreacted formaldehyde.

Example 1

Pre-Heating 90% of Formaldehyde

Approximately 10.18 g of 52 wt % aqueous solution of formaldehyde (<1% methanol, DuPont) was mixed with 12.81 g of water, and the slurry was heated to about 76° C. for about 40 min until the mixture became a clear homogeneous liquid solution. The solution was allowed to cool to ambient temperature and remained a homogeneous liquid. 0.16 mL of 16.7 wt % aqueous NaOH solution was then added to the formaldehyde solution. 1.56 g of the resulting solution (23 wt % formaldehyde) was placed in the reaction vessel, and the remainder was used for the continuous formaldehyde feed.

The reaction vessel, equipped with stirring, was placed within an oil bath maintained at 55° C. The approximately 12-inch section of the formaldehyde feed line (1/16" OD (about 1.6 mm)×0.040" ID (about 1.02 mm)) directly preceding the inlet to the reaction flask was heated to 120° C., and the reactants were then each continuously pumped into the reaction vessel over a period of about 2.0 hr, as follows:

4.41 mL/hr of 50 wt % aqueous HCN solution (d=0.86 g/mL)

7.00 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.08 mL of 37 wt % aqueous HCl.

Figure 2:
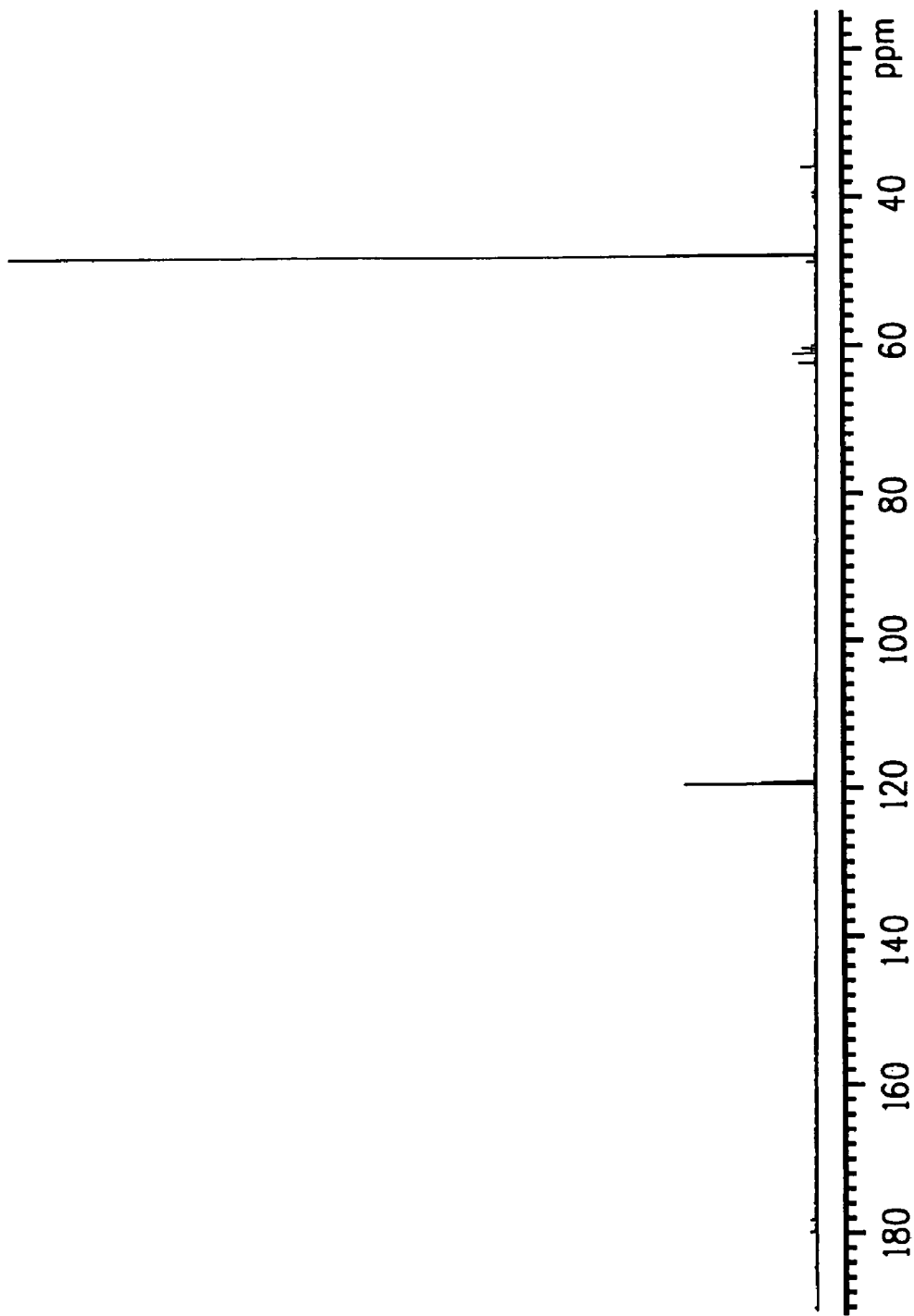
FIG. 2 shows $^{13}$C NMR spectrum of the resulting glycolonitrile solution from Example 1, qualitatively indicating the purity of the glycolonitrile product. The major resonances for glycolonitrile at about δ48 and 119 ppm are observed. The resonances around δ80-90 ppm evident in FIG. 1 for unreacted formaldehyde are noticeably reduced in FIG. 2. However, the resonances around δ60 ppm for by-products derived from unreacted formaldehyde remain, most likely due to the initial formaldehyde reactor charge.

FIG. 2 shows the $^{13}$C NMR spectrum of the resulting glycolonitrile solution, qualitatively indicating the purity of the glycolonitrile product. Once again, the major resonances for glycolonitrile at about δ48 and 119 ppm are observed. But the resonances around δ80-90 ppm evident in FIG. 1 for unreacted formaldehyde are noticeably reduced in FIG. 2. However, the resonances around δ60 ppm for by-products derived from unreacted formaldehyde remain, most likely due to the initial formaldehyde reactor charge.

Example 2

Pre-Heating 100% of Formaldehyde

Approximately 10.18 g of 52 wt % aqueous solution of formaldehyde (<1% methanol, E.I. DuPont de Nemours) was mixed with 12.81 g of water, and the slurry was heated to about 76° C. for about 40 min until the mixture became a clear homogeneous liquid solution. The solution was allowed to cool to ambient temperature and remained a homogeneous liquid. 0.14 mL of 16.7 wt % aqueous NaOH solution was then added to the formaldehyde solution. The resulting solution (23 wt % formaldehyde) was used for the continuous formaldehyde feed.

The reaction vessel, equipped with stirring, was charged with a mixture of 0.18 g of HCN in 3.4 g of water and then placed within an oil bath maintained at 55° C. The approximately 12-inch section of the formaldehyde feed line (1/16" OD×0.040" ID) directly preceding the inlet to the reaction flask was heated to 120° C., and the reactants were then each continuously pumped into the reaction vessel over a period of about 2.0 hr, as follows:

4.41 mL/hr of 50 wt % aqueous HCN solution (d=0.86 g/mL)

7.67 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

Figure 3:
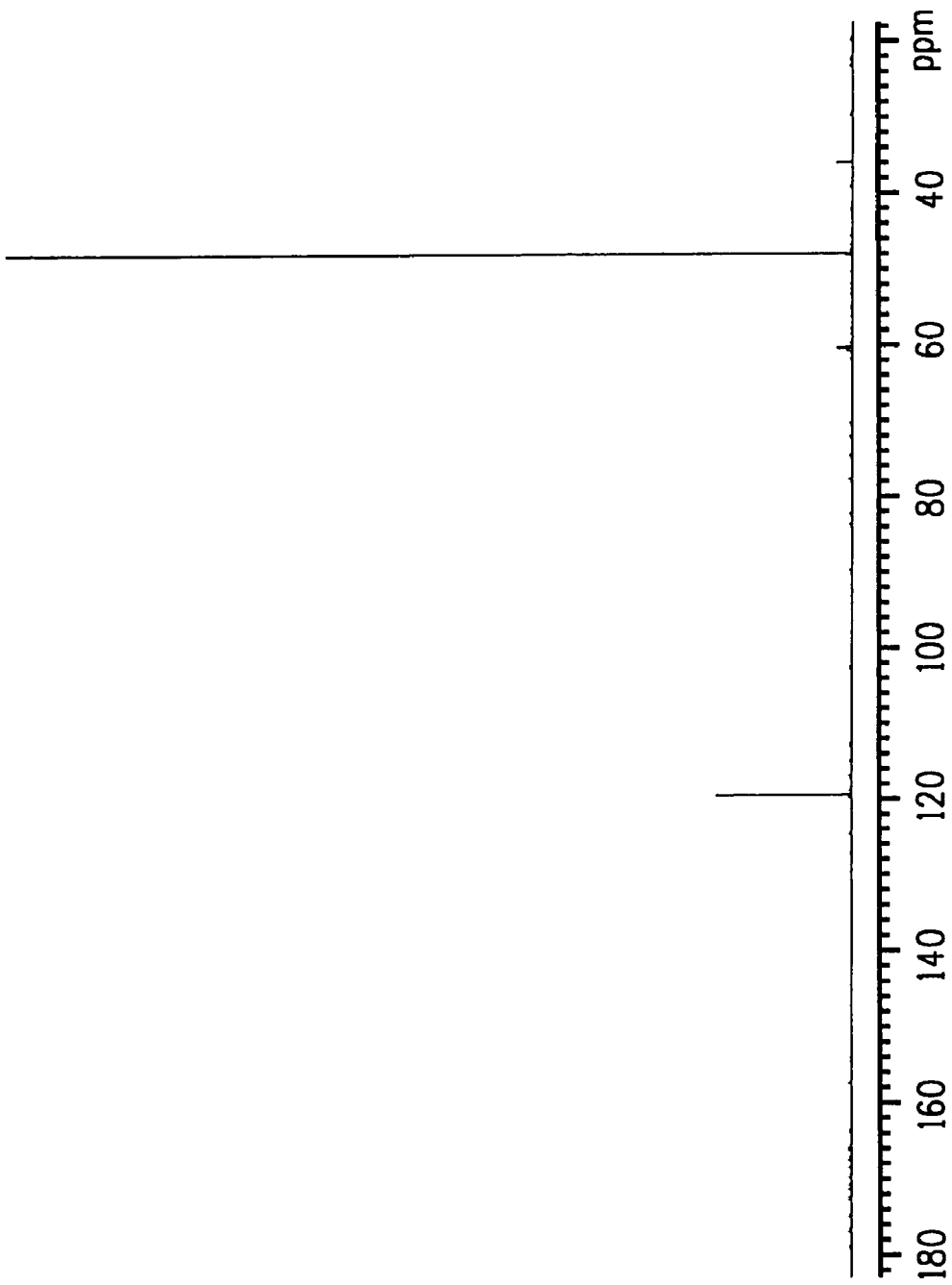
FIG. 3 shows $^{13}$C NMR spectrum of the resulting glycolonitrile solution from Example 2, qualitatively indicating the purity of the glycolonitrile product. The major resonances for glycolonitrile at about δ48 and 119 ppm are evident in FIG. 3, while the levels of impurities are substantially reduced from the levels observed in FIG. 1 and FIG. 2.

FIG. 3 shows the $^{13}$C NMR spectrum of the resulting glycolonitrile solution, qualitatively indicating the purity of the glycolonitrile product. The major resonances for glycolonitrile at about δ48 and 119 ppm are evident in FIG. 3, while the levels of impurities are substantially reduced from the levels observed in FIG. 1 and FIG. 2.

Example 3

Pre-Heating 100% of Formaldehyde

Approximately 14.20 g of 37 wt % aqueous solution of formaldehyde (10-15% methanol, Acros Organics, Morris Plains, N.J.) was mixed with 8.78 g of water and 0.14 mL of 16.7 wt % aqueous NaOH. The resulting solution (23 wt % formaldehyde) was used for the continuous formaldehyde feed.

The reaction vessel, equipped with stirring, was charged with a mixture of 0.18 g of HCN in 3.4 g of water and then placed within an oil bath maintained at 55° C. The approximately 12-inch section of the formaldehyde feed line (1/16" OD×0.040" ID) directly preceding the inlet to the reaction flask was heated to 120° C., and the reactants were then each continuously pumped into the reaction vessel over a period of about 2.0 hr, as follows:

4.21 mL/hr of 50 wt % aqueous HCN solution (d=0.86 g/mL)

7.67 mL/hr of 23 wt % aqueous formaldehyde, described above (d=1.07 g/mL).

After about 2.0 hr, the feeds were stopped, the reaction vessel was removed from the oil bath, and the reaction mixture was quenched with the addition of 0.07 mL of 37 wt % aqueous HCl.

Figure 4:
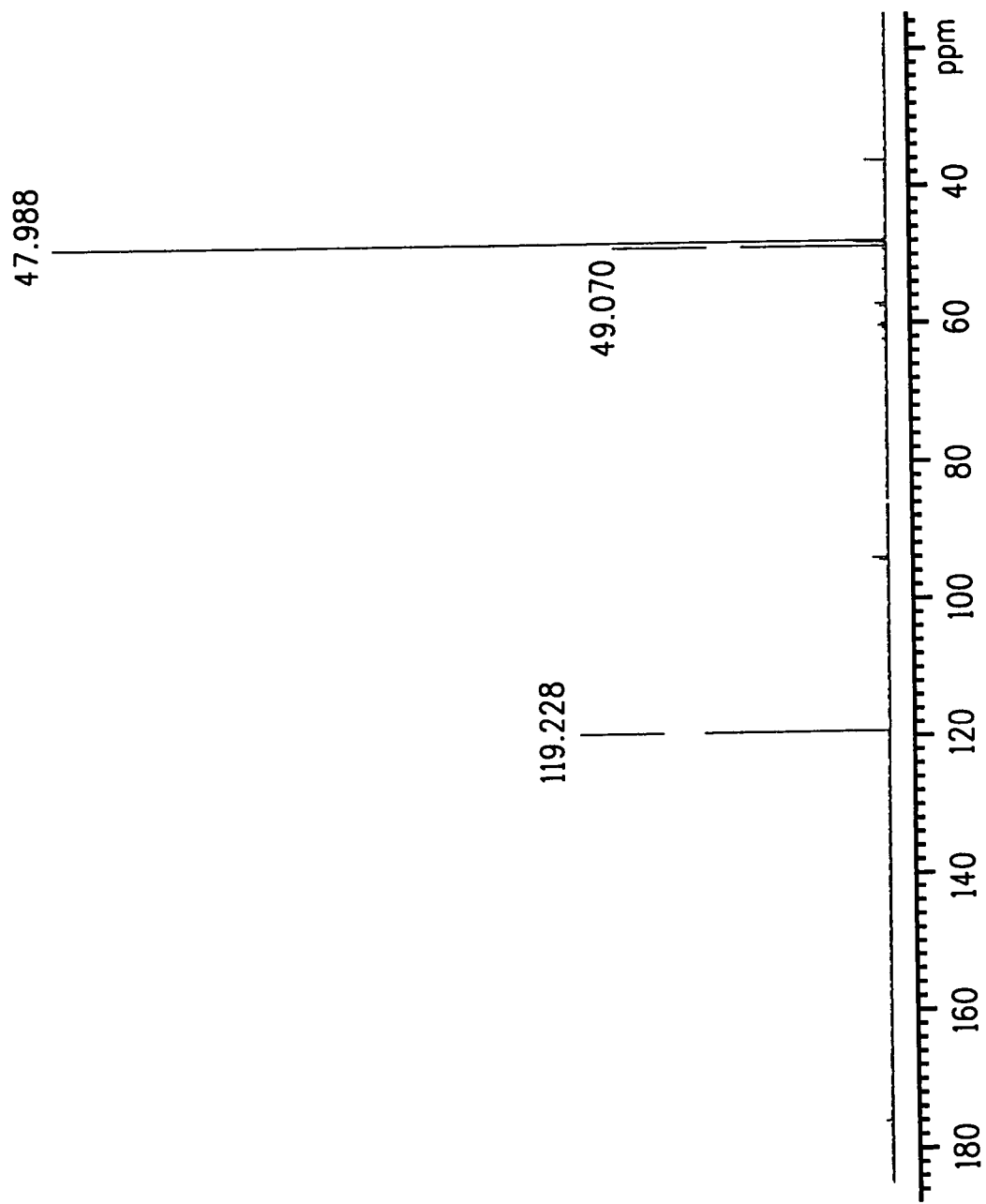
FIG. 4 shows $^{13}$C NMR spectrum of the resulting glycolonitrile solution from Example 3, qualitatively indicating the purity of the glycolonitrile product. The major resonances for glycolonitrile at about δ48 and 119 ppm are evident in FIG. 4, while the levels of impurities are substantially reduced from the levels observed in FIG. 1 and FIG. 2.

FIG. 4 shows the $^{13}$C NMR spectrum of the resulting glycolonitrile solution, qualitatively indicating the purity of the glycolonitrile product. Again, the major resonances for glycolonitrile at about δ48 and 119 ppm are evident in FIG. 4, while the levels of impurities are substantially reduced from the levels observed in FIG. 1 and FIG. 2. FIG. 4 also clearly shows the resonance at δ49 ppm for the methanol from the formalin feed used in Example 3.

Examples 4-8

Pre-Heating 100% of Formaldehyde

In Examples 4-8, the following glycolonitrile synthesis procedure was repeated five separate times.

Approximately 0.56 mL of 16.7 wt % aqueous NaOH solution was added to 218.0 g of 37 wt % aqueous solution of formaldehyde (containing 7 wt % to 8 wt % methanol). The resulting solution was used for the continuous formaldehyde feed.

The reaction vessel, equipped with a magnetic stirbar, was initially charged with a mixture of 3.3 g HCN in 35.3 g water and placed within a water bath maintained at around 20° C., on top of a stirplate and lab jack assembly in a lowered position. The approximately 36-inch section of the formaldehyde feed line (1/8" OD (about 3.18 mm)×0.085" ID (about 2.16 mm)) directly preceding the inlet to the reaction flask was heated to 120° C. after filling the formaldehyde feed line, and the flow of heated formaldehyde feed was first established by observing two-phase flow from the outlet of the formaldehyde feed line. After establishing two-phase flow out of the formaldehyde feed line, the reaction vessel was raised to introduce the formaldehyde feed directly into the liquid reaction mixture. The stirplate, water bath, and lab jack assembly was then raised accordingly to provide reactor mixing and to maintain the reaction temperature around 20-25° C., which was accomplished by periodically adding ice and/or dry ice to the external water bath.

The reactants were each continuously pumped into the reaction vessel over a period of about 2.0 hr, as follows:

82.4 mL/hr of 50 wt % aqueous HCN solution (d=0.86 g/mL)

92.7 mL/hr of 37 wt % aqueous formaldehyde, described above (d=1.09 g/mL).

After 2.0 hr, the feeds were stopped, and the reaction vessel, water bath, stirplate, and lab jack assembly was lowered to remove the formaldehyde feed line from the reaction product. The reaction mixture was removed from the reaction vessel and then quenched by adding of 1.3 mL of an aqueous solution of 70% glycolic acid (70% Glypure®; E.I. DuPont de Nemours, Wilmington, Del.), resulting in a glycolonitrile product solution at about pH 3.

Each of the glycolonitrile reaction product solutions was individually concentrated to remove the excess unreacted HCN and the methanol from the commercial source of formaldehyde. The concentration step was performed under vacuum with mild heating using an external oil bath at 60-70° C.

The weight of each concentrated glycolonitrile product solution was recorded, and the glycolonitrile concentration was determined by HPLC.

The conditions used in Examples 4-8, and the resulting GLN yield is reported in Table 1.

TABLE 1

Glycolonitrile yield.

| Example # | Weight of GLN Solution (g) | Glycolonitrile Concentration (M) | Yield (% recovered GLN) |
|---|---|---|---|
| 4 | 116 | 13.9 | 61% |
| 5 | 139 | 17.7 | 94% |
| 6 | 163 | 13.7 | 85% |
| 7 | 150 | 16.7 | 95% |
| 8 | 182 | 11.6 | 80% |

Figure 5:
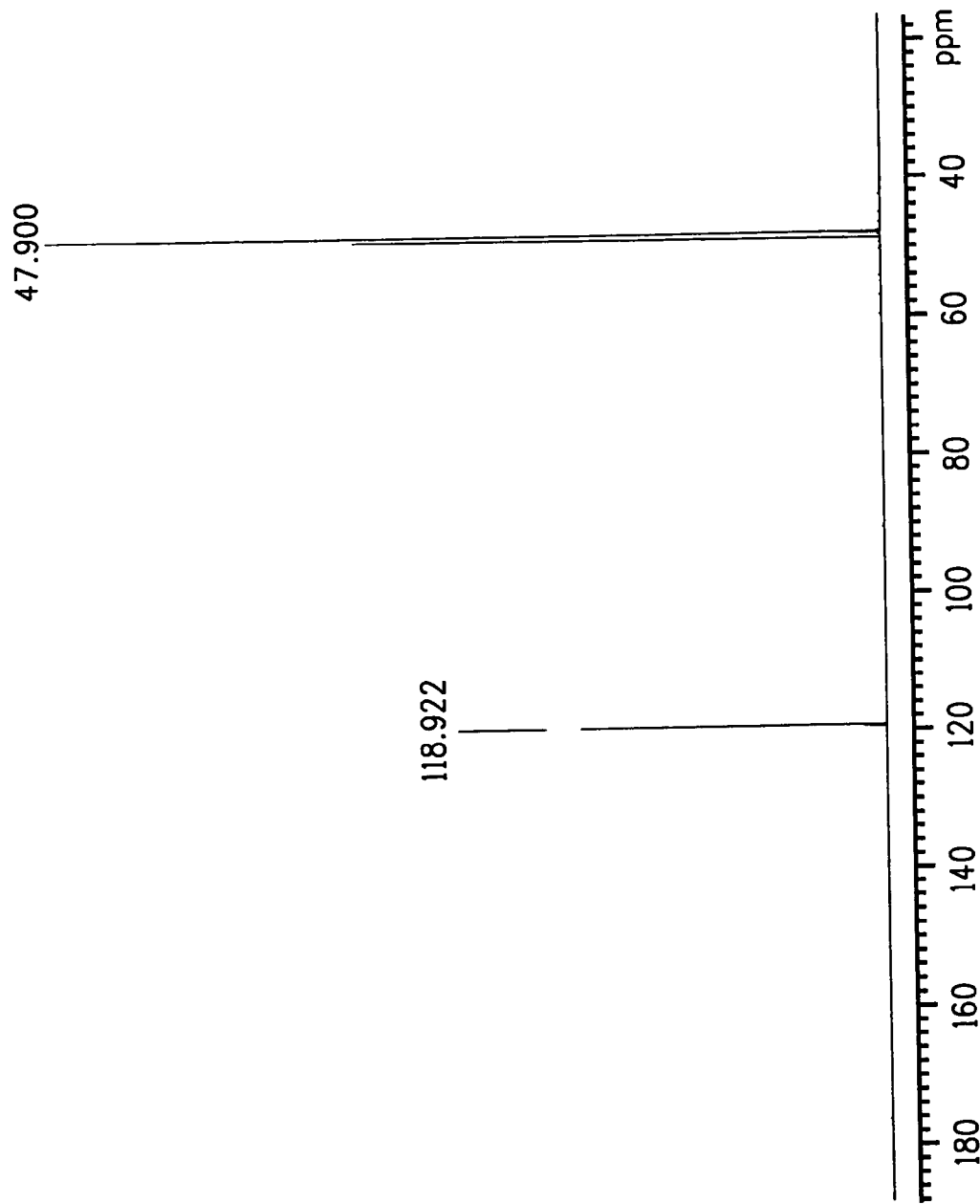
FIG. 5 shows the $^{13}$C NMR spectrum of the composite sample produced by mixing the 5 concentrated glycolonitrile samples prepared in Examples 4-8, quantitatively indicating the purity of the glycolonitrile product. The quantitative $^{13}$C NMR analysis was performed on the composite sample to determine the purity of the glycolonitrile produced.

The five concentrated glycolonitrile product solutions produced in Examples 4-8 were combined into a composite product sample, and a quantitative $^{13}$C NMR analysis was performed on the composite sample to determine the purity of the glycolonitrile produced. FIG. 5 shows the $^{13}$C NMR spectrum of the composite sample. The quantitative $^{13}$C NMR analysis showed that the glycolonitrile product purity was greater than 99.0% in the composite sample.

Example 9

Pre-Heating 100% of Formaldehyde

Approximately 0.27 mL of 16.7 wt % aqueous NaOH solution was added to 54.5 g of 37 wt % aqueous solution of formaldehyde (containing 7-8% methanol). The resulting solution was used for the continuous formaldehyde feed.

The reaction vessel, equipped with a magnetic stirbar, was initially charged with a mixture of 0.29 g HCN in 10.3 g water and placed within a water bath maintained at around 25° C., on top of a stirplate. The approximately 12-inch section of the formaldehyde feed line (⅛" OD×0.085" ID) directly preceding the inlet to the reaction flask was heated to 150° C. after filling the formaldehyde feed line, and the flow of heated formaldehyde feed was first established outside the reaction vessel by observing two-phase flow from the outlet of the formaldehyde feed line. After establishing heated formaldehyde feed, the end of the formaldehyde feed line was placed directly into the liquid reaction mixture. The reaction temperature was maintained around 20-25° C., which was accomplished by periodically adding ice and/or dry ice to the external water bath. The reactants were each continuously pumped into the reaction vessel over a period of about 2.0 hr, as follows:

7.02 mL/hr of 50 wt % aqueous HCN solution (d=0.86 g/mL)

7.67 mL/hr of 37 wt % aqueous formaldehyde, described above (d=1.09 g/mL).

After 2.0 hr, the feeds were stopped, and the formaldehyde feed line was removed from the reaction product. The reaction mixture was removed from the reaction vessel and then quenched by adding of 0.060 mL of 70% Glypure® glycolic acid, resulting in a glycolonitrile product solution at about pH 3.

Figure 6:
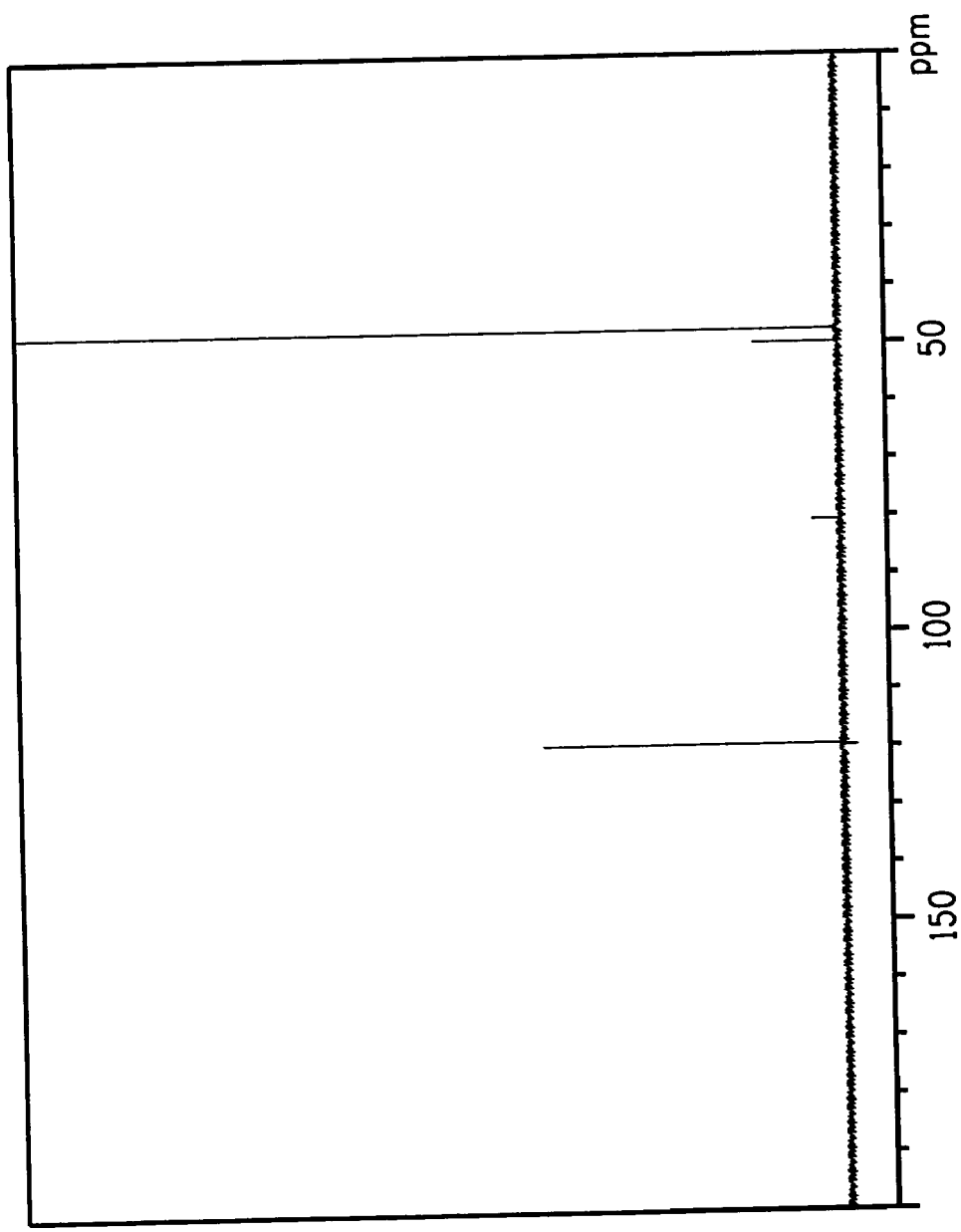
FIG. 6 shows $^{13}$C NMR spectrum of the resulting glycolonitrile solution, qualitatively indicating the purity of the glycolonitrile product produced in Example 9.

FIG. 6 shows the $^{13}$C NMR spectrum of the resulting glycolonitrile solution, qualitatively indicating the purity of the glycolonitrile product.

Example 10

Pre-Heating 100% of Formaldehyde

Approximately 0.40 mL of 16.7 wt % aqueous NaOH solution was added to 58.0 g of 37 wt % aqueous solution of formaldehyde (containing 7-8% methanol). The resulting solution was used for the continuous formaldehyde feed.

The reaction vessel, equipped with a magnetic stirbar, was initially charged with a mixture of 0.29 g HCN in 10.3 g water and placed within a water bath maintained at around 25° C., on top of a stirplate. The approximately 24-inch section of the formaldehyde feed line (⅛" OD×0.085" ID) directly preceding the inlet to the reaction flask was heated to 90° C. after filling the formaldehyde feed line. After establishing heated formaldehyde feed outside of the reaction vessel, the end of the formaldehyde feed line was placed directly into the liquid reaction mixture. The reaction temperature was maintained around 20-25° C., which was accomplished by periodically adding ice and/or dry ice to the external water bath. The reactants were each continuously pumped into the reaction vessel over a period of about 2.0 hr, as follows:

7.02 mL/hr of 50 wt % aqueous HCN solution (d=0.86 g/mL)

7.67 mL/hr of 37 wt % aqueous formaldehyde, described above (d=1.09 g/mL).

Figure 7:
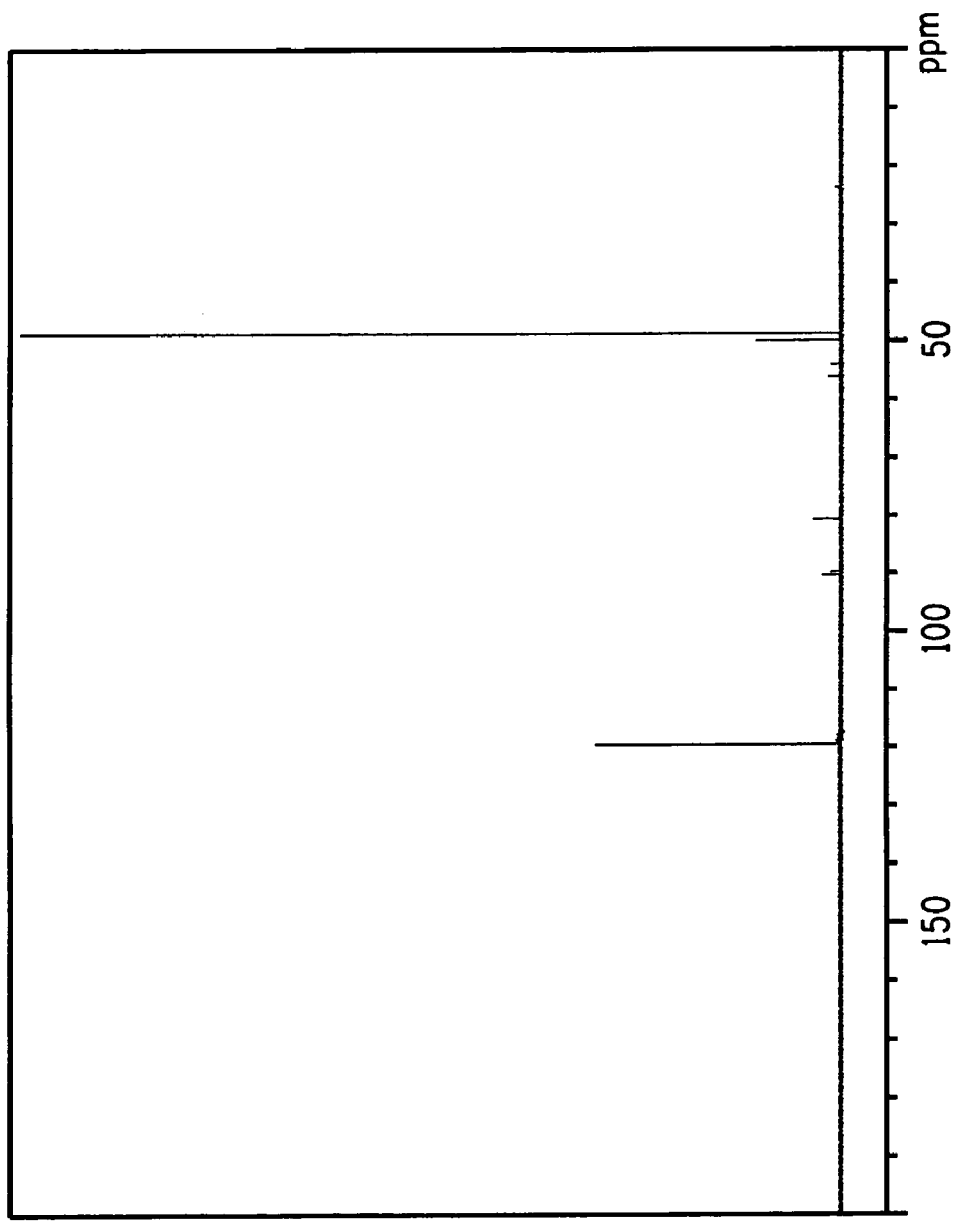
FIG. 7 shows $^{13}$C NMR spectrum of the resulting glycolonitrile solution, qualitatively indicating the purity of the glycolonitrile product produced in Example 10.

After 2.0 hr, the feeds were stopped, and the formaldehyde feed line was removed from the reaction product. The reaction mixture was removed from the reaction vessel and then quenched by adding of 0.10 mL of 70% Glypure® glycolic acid, resulting in a glycolonitrile product solution at about pH 3-4. FIG. 7 shows the $^{13}$C NMR spectrum of the resulting glycolonitrile solution, qualitatively indicating the purity of the glycolonitrile product.

What is claimed is:

1. A method for preparing glycolonitrile comprising:
   a) providing an aqueous formaldehyde feed stream that is heated to a temperature of about 90° C. to about 150° C. for a determinable period of time; and
   b) reacting the heated aqueous feed stream of (a) with hydrogen cyanide at a temperature suitable for glycolonitrile synthesis, whereby glycolonitrile is produced.

2. The method of claim 1, further comprising recovering the glycolonitrile produced in step (b).

3. The method of claim 1 wherein an amount sodium hydroxide is added to the aqueous formaldehyde feed stream prior to heating the aqueous formaldehyde feed stream wherein the molar ratio of sodium hydroxide to formaldehyde is about 1:50 to about 1:2000.

4. The method of claims 1, 2, or 3 further comprising adding an acid to the glycolonitrile produced in step (b) to form a stabilized glycolonitrile solution.

5. The method of claim 4, wherein the acid is glycolic acid.

6. The method of claim 4 or claim 5 wherein the stabilized glycolonitrile solution has a pH of less than 7.

7. The method of claim 6 wherein the stabilized glycolonitrile solution has a pH of less than about 4.

8. The method of claim 1 wherein the molar ratio of hydrogen cyanide to formaldehyde is at least 1.01:1.

9. The method of claim 8 wherien the molar ratio of hydrogen cyanide to formaldehyde is at least 1.01:1 to about 1.15:1.

10. The method of claim 1 wherein the aqueous formaldehyde feed stream further comprises about 0.1 wt % to about 15 wt % methanol.

11. The method according to claim 1 wherein the aqueous formaldehyde feed stream further comprises about 3 wt % to about 8 wt % methanol.

12. The method according to claim 1 wherein said temperature suitable for glycolonitrile synthesis is about 0° C. to about 70° C.

13. The method according to claim 12 wherein said temperature suitable for glycolonitrile synthesis is about 10° C. to about 30° C.

14. The method according to claim 1 wherein the aqueous formaldehyde feed stream is heated for a period of time from about 10 seconds to about 24 hours.

15. The method according to claim 14 wherein the period of time is about 10 seconds to about 20 minutes.

16. The method according to claim 15 wherein the aqueous formaldehyde feed stream is heated for a period of time from about 2 minutes to about 10 minutes.

17. The method of claim 1 wherein the resulting aqueous solution of glycolonitrile comprises less unreated formaldehyde compared to a reaction product obtained without heating the aqueous formaldehyde feed stream prior to reacting with hydrogen cyanide.

18. The method of claim 1, wherein the glycolonitrile produced may be used for enzymatic conversion to ammonium glycolate without purification.

* * * * *